United States Patent [19]

Nava

[11] Patent Number: 5,679,871
[45] Date of Patent: Oct. 21, 1997

[54] HYDROXYALKLYLATION OF PHENOLS

[75] Inventor: Hildeberto Nava, Cary, N.C.

[73] Assignee: Reichhold Chemicals, Inc., Durham, N.C.

[21] Appl. No.: 718,978

[22] Filed: Sep. 26, 1996

[51] Int. Cl.$^6$ .................... C07C 43/16; C07C 319/02
[52] U.S. Cl. .................... 568/648; 568/55; 568/45
[58] Field of Search ................ 568/55, 45, 648; 558/260

[56] References Cited

U.S. PATENT DOCUMENTS

| | | | |
|---|---|---|---|
| 3,549,692 | 12/1970 | Bockman | 260/475 |
| 3,553,167 | 1/1971 | Schnell et al. | 260/17 |
| 4,107,143 | 8/1978 | Inata et al. | 528/176 |
| 4,216,298 | 8/1980 | Schreckenberg et al. | 525/439 |
| 4,217,297 | 8/1980 | Lindner et al. | 260/463 |
| 4,261,922 | 4/1981 | Kem | 260/512 R |
| 4,297,455 | 10/1981 | Lindner et al. | 525/439 |
| 4,310,706 | 1/1982 | Strege | 568/648 |
| 4,310,707 | 1/1982 | Strege | 568/648 |
| 4,310,708 | 1/1982 | Strege et al. | 568/648 |
| 4,341,905 | 7/1982 | Strege | 568/45 |
| 4,355,136 | 10/1982 | Dombroski et al. | 525/35 |
| 4,388,455 | 6/1983 | Bales | 528/176 |
| 4,584,408 | 4/1986 | Wang et al. | 568/48 |
| 4,613,678 | 9/1986 | Swart | 560/92 |
| 5,059,723 | 10/1991 | Dressler | 568/640 |
| 5,068,460 | 11/1991 | Sumner, Jr. et al. | 568/648 |
| 5,304,628 | 4/1994 | Kinoshita et al. | 528/370 |
| 5,442,037 | 8/1995 | Lee et al. | 528/301 |
| 5,451,656 | 9/1995 | Menovcik et al. | 528/288 |

FOREIGN PATENT DOCUMENTS

WO 91/16292  4/1991  WIPO ...................... C07C 41/16

OTHER PUBLICATIONS

CA:116 :173663 A, Mustafaer –Synthesis and some transformation of 1–aryl elhirs of 1,2–octanedirl ZH Org Khim (1991) 27(7) 1402–7.

*Primary Examiner*—C. Warren Ivy
*Assistant Examiner*—Jean F. Vollano
*Attorney, Agent, or Firm*—Bell, Seltzer, Park & Gibson

[57] ABSTRACT

A process for the production of hydroxyalkylated phenolic or hydroxyalkylated thiophenolic compounds is disclosed. The process comprises providing a phenolic or thiophenolic compound, a cyclic organic carbonate compound, and a catalyst selected from the group consisting of an alkali metal, an alcohol-derived salt of the alkali metal, and mixtures thereof; and reacting the phenolic compound and the cyclic organic carbonate compound in the presence of the catalyst to form the hydroxyalkylated phenolic or hydroxyalkylated thiophenolic compound. Preferably, the alkali metal is selected from sodium, potassium, or lithium.

12 Claims, No Drawings

HYDROXYALKLYLATION OF PHENOLS

FIELD OF THE INVENTION

The present invention relates to a process for the preparation of hydroxyalkylated compounds. More particularly, the invention relates to a process for the preparation of a hydroxyalkylated phenolic or hydroxyalkylated thiophenolic compound from a phenolic or thiophenolic compound and a cyclic organic carbonate compound.

BACKGROUND OF THE INVENTION

Hydroxyalkylated phenolic and thiophenolic compounds are primarily useful as intermediates in various chemical processes. In particular, the compounds are useful in the preparation of unsaturated polyesters, especially those employed in applications which require corrosion resistance. In general, two types of processes are often used in the preparation of hydroxyalkylated phenols. The first process involves the reaction of a phenolic or thiophenolic compound with an organic oxide such as ethylene oxide or propylene oxide under pressure. This process, however, suffers from several drawbacks. Specialized equipment must be employed to accommodate the high pressures under which the reaction takes place. Moreover, adequate safety precautions must be taken due to the organic oxide starting materials.

The second type of process involves the reaction of phenolic compounds with cyclic organic carbonates in the presence of various catalysts. For example, U.S. Pat. Nos. 2,967,892 to Smith; 4,261,922 to Kem; 4,310,707 and 4,341,905 Strege to generally propose the use of alkyl metal salt catalysts. U.S. Pat. Nos. 4,310,708 to Strege et al. and 5,059,723 to Dressler propose using phosphorous-type catalysts. U.S. Pat. No. 4,310,706 to Strege proposes utilizing an imidazole catalyst in the preparation of hydroxyalkylated phenols.

The above catalysts suffer from several drawbacks. For example, alkyl metal salts have been found to be insoluble in the final end products and also adversely effect the end products' oxidative stability. Moreover, imidazole catalysts have been found to contribute to the formation of highly colored hydroxy alkylated products. Phosphorous-type catalysts generally yield complexes which exhibit high coloration when mixed with carboxylic acid and anhydride monomer such as in the preparation of saturated and unsaturated polyesters.

In view of the above, it is an object of the present invention to provide a catalyst to be utilized in the reaction of a phenolic or thiophenolic compound and a cyclic organic carbonate to form a hydroxyalkylated phenol or hydroxyalkylated thiophenol compound which minimizes the adverse effects associated with the catalysts described above.

SUMMARY OF THE INVENTION

The present invention provides a process for the preparation of a hydroxyalkylated phenol or hydroxyalkylated thiophenol compound which addresses the problems stated above. The process comprises providing a phenol or thiophenol compound, a cyclic organic carbonate, and a catalyst selected from the group consisting of metals, alcohol-derived salts of metals, and mixtures thereof; and reacting the phenol or thiophenol compound and the cyclic organic carbonate compound in the presence of the catalyst to form the hydroxyalkylated phenol or hydroxyalkylated thiophenol compound.

As described in greater detail herein, the metals utilized in the catalyst are in substantially pure form, and are preferably selected from the group consisting of sodium, potassium, and lithium. Alcohol-derived salts of the above metals (i.e., alkali metal alkoxides) may also be employed and include methoxide and ethoxide salts thereof.

The phenolic compounds are preferably selected from the group consisting of phenol, β-naphthol, p,p'-sec-butylidene diphenol, o-chloro phenol, o-cresol, p-propyl phenol, p-bis(o-cresol), phenyl phenol, thiophenol, o-thiocresol, m-thiocresol, p-thiocresol, 4,4'-thiodiphenol, 4,4'-thiobisbenzenethiol, hydroxyquinoline, catechol, resorcinol, hydroquinone, 4,4'-biphenol, 4,4'-isopropylidenebis(o-cresol), 4,4'-isopropylidenebis(2-phenyl phenol), bisphenol A, nonyl phenol, pyrogallol, phloroglucinol, and mixtures thereof.

The cyclic organic carbonates are preferably selected from the group consisting of propylene carbonate, 1,2-butylene carbonate, 2,3-butylene carbonate, phenylethylene carbonate, and mixtures thereof.

DETAILED DESCRIPTION OF THE PREFERRED EMBODIMENTS

As summarized above, the present invention relates to a process for the preparation of a hydroxyalkylated phenol or hydroxyalkylated thiophenol compound. Specifically, the process includes providing a phenolic or thiophenolic compound, a cyclic organic carbonate, and a catalyst selected from alkali metals, alcohol-derived salts of the metals and mixtures thereof; and reacting the phenolic or thiophenolic compound and the cyclic organic carbonate in the presence of the catalyst to form the hydroxyalkylated phenol or hydroxyalkylated thiophenol compound.

The phenolic or thiophenolic compounds which may be employed are numerous and known in the art. Exemplary compounds along with a description of such may be found in U.S. Pat. Nos. 4,310,708 to Strege et al. and 5,059,723 to Dressler, the disclosures of which are incorporated by reference in their entirety. Compounds which are suitable for the purposes of the invention may be represented by the following formulae:

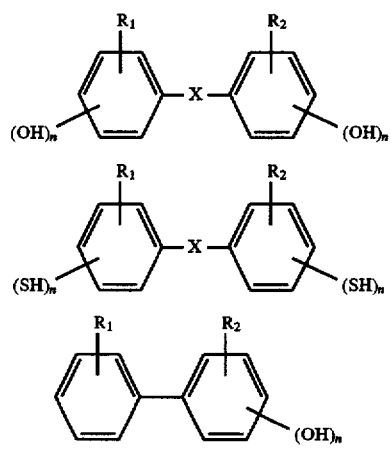

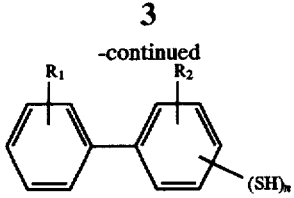

wherein X may be —O—, —S—, —SO$_2$—, or —CO—; R$_1$ and R$_2$ may be hydrogen, alkyl or aryl; and n may be an integer from 1 to 5. Examples of monohydric phenols which may be employed generally include phenol, β-naphthol, p,p'-sec-butylidenediphenol, o-chloro phenol, o-cresol, p-propyl phenol, p-bis(o-cresol), phenyl phenol, nonyl phenol, mono-, di-, and tri-alkyl phenols, C$_1$ to C$_{18}$ substituted phenols, polyaralkylphenols, halophenols, arylphenols, naphthols and hydroxyquinoline. Examples of some useful di- and polyhydric phenols include catechol; resorcinol; hydroquinone; 4,4'-biphenol; 4,4'-isopropylidenebis(o-cresol); 4,4'-isopropylidenebis(2-phenyl phenol); alkylidenediphenols such as bisphenol A, pyrogallol, and phloroglucinol; naphthalenediols; phenol/formaldehyde resins; resorcinol/formaldehyde resins; and phenol/resorcinol/formaldehyde resins. Exemplary thiophenols include thiophenol, o-thiocresol, m-thiocresol, p-thiocresol, 4,4'-thiodiphenol, and 4,4'-thiobisbenzenethiol. Alkaline salts of phenols may also be used. Mixtures of any of the above compounds can be employed in the process. The phenol or thiophenol compound may be employed in any suitable amount in the process.

Numerous cyclic organic carbonate compounds may be used in the invention, including those described in the references cited above as well as U.S. Pat. No. 2,987,555 to Davis, the disclosure of which is incorporated by reference it its entirety. In general, suitable organic carbonate compounds include any cyclic alkylene carbonate having the appropriate carbonate moiety attached at adjacent positions is capable of undergoing hydroxyalkylation with the phenolic or thiophenolic compounds. Particularly suitable cyclic organic carbonates are of the general formula:

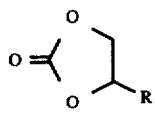

where R is selected from the group consisting of H, C$_1$-C$_{18}$ alkyl, C$_1$-C$_{20}$ alkoxy, alkoxyalkylene, (poly) alkoxyalkylene, and aryl. Specific examples of cyclic organic carbonates include, but are not limited to, propylene carbonate, 1,2- and 2,3-butylene carbonate, and phenylethylene carbonate. Mixtures of any of the above compounds may be employed. The cyclic organic carbonate may be employed in any suitable amount in the process.

The catalyst which is to be employed in the hydroxyalkylation reaction may be selected from an alkali metal, an alcohol-derived salt of the alkali metal, and mixtures thereof. For the purposes of the invention, the alkali metal is to be utilized in substantially pure form. For the purposes of the invention, the alkali metal catalyst in "substantially pure form" means a metal existing as an uncombined chemical element. Sodium metal is preferred as a catalyst. The alcohol-derived salt which may be employed, includes for example, methoxide and ethoxide salts of the above metals. Preferred alcohol-derived salts are sodium methoxide and sodium ethoxide. The metal or alcohol-derived salt catalyst may be used alone or in combination with other catalysts such as, but not limited to, triorgano phosphine compounds (e.g., triphenyl phosphine, tributyl phosphine, diphenylbutyl phosphine, and dibutyl phosphine); phosphonium salts (e.g., triphenyl phosphonium bromide, triphenyl phosphonium acetate, tributyl phosphonium bromide, tributyl phosphonium acetate); imidazoles (e.g., imidazole, 2-methylimidazole, N-(2'-hydroxyethyl)-2-methylimidazole, piperidine, morpholine, triethylamine); tertiary amine compounds and their salts (e.g., triethyl amine and tributyl amine); and organometallic salts (e.g., zinc octoate, magnesium octoate, zirconium hexanoate). The catalyst may be used in various amounts in the process. Typically as is known to one skilled in the art, this amount will vary depending on the type of phenolic or thiophenolic compound, cyclic organic carbonate, and catalyst used. Reaction conditions such as temperature and pressure also may influence catalyst amount. The amount of catalyst is preferably between about 0.005 and 3.0 percent by weight based on the total amount of reacting components. More preferably, the catalyst will be between about 0.01 to 1.0 percent by weight.

Additional components which are known to be used in hydroxyalkylation reactions may be utilized in the process. As an example, the reaction may take place in the presence of an appropriate inert solvent such as, for example, toluene, xylene, cyclohexane, tetrahydronaphthalene, naphthalene, anisole, and chlorobenzene. The use of a solvent will typically depend on its properties and on the types of phenolic compound, cyclic organic carbonate, and catalyst used. Typically, the addition of a solvent is not necessary for carrying out the reaction.

The process may be carried out using various molar ratios of the cyclic organic carbonate compound to the phenolic compound. Preferably, the cyclic organic carbonate may be added in excess ranging from about 1.02 to 1.50 moles per every hydroxyl or thiol group in present in the phenol moieties. More preferably, the excess of cyclic carbonate will be between about 1.05 to 1.25 mole per every hydroxy or thiol group present in the phenol or thiophenol moieties. It is believed that the use of excess of cyclic organic carbonate compound is to assure complete formation of the phenolic or thiophenolic compound. In the event that an excess of cyclic organic carbonate compound is used, the amount present after the reaction may optionally be removed by vacuum distillation. In most applications, such as in the preparation of polyurethanes, saturated and unsaturated polyesters, the removal of cyclic carbonate is not required.

The process of the invention may be carried out in any known and suitable vessel which is designed to contain the reactants and products, including those described in U.S. Pat. No. 4,310,708 to Strege et al. Preferably, the materials of the vessel are inert under the conditions employed during the process. Such materials may include glass, stainless steel, and the like.

The reaction may be run at any suitable temperature, preferably from about 100° C. to 220° C., and more preferably from about 150° C. to 200° C. It is believed that the reaction rate of the hydroxyalkylation reaction is temperature dependent, with faster rates being observed at higher temperatures and the decomposition of reactants and products likely to occur at higher temperatures. Accordingly, the optimum operating temperature for any reaction may be determined by the skilled artisan through experimentation. Heating of the reaction vessel to the operating temperature may be achieved by any suitable means such as a heat lamp, heating mantle, oil bath, and the like.

The reaction time to obtain adequate conversion of the phenolic or thiophenolic compound will typically vary depending on various factors such as, for example, temperature, catalyst type, type of phenolic compound and cyclic organic carbonate. Generally, the time which is sufficient for the reaction to take place is from about 5 and 12 hours. The reaction can be followed by the consumption of the phenolic compound by analytical titration methods as described in R. W. Martin, *Analytical Chemistry*, 21, 1419 (1949).

Additional means may be employed to facilitate the reaction of the phenolic or thiophenolic compound and the cyclic organic carbonate. For example, the reaction may proceed with or without stirring by mechanical, magnetic or other known means. In addition, to avoid liquid entrapment during the evolution of carbon dioxide during the reaction, it is preferred to employ a suitable condenser.

The hydroxyalkylated phenolic or hydroxyalkylated thiophenolic compound produced in accordance with the invention may be used as is or may be purified by any of the well known techniques including fractional distillation or crystallization.

The following examples are provided to illustrate the present invention, and should not be construed as limiting thereof.

EXAMPLE 1

Preparation of Hydoxyalkylated Phenol Using a Sodium Metal Catalyst

A 2000 ml reactor was charged with 685 grams (3.0 moles) of bisphenol "A", 546 grams (6.20 moles) of propylene carbonate and 0.25 grams of sodium metal. The mixture was stirred and the temperature increased to 175° C. The reaction was followed by titration analysis of the consumption of phenol and stopped until complete conversion. The product was analyzed by $H^1$ NMR and identified as the hydroxypropyl derivative of Bisphenol "A" with NMR ($CDCl_3$, TMS) analysis as follows: 6.85 ppm, 7.15 ppm (8H, Ar—), 4.5 ppm (Ar—O—CH), 4.2 ppm (—CH—O—), 3.8 ppm (—$CH_2$—), 1.7 ppm (—$CH_3$—), 1.3 ppm (—$(CH_3)_2$—C—). The Brookfield viscosity of the hydroxyalkylated phenol was determined using standard procedure at 40° C. to be 40 poise.

EXAMPLE 2

Preparation of a Hydroxyalkylated Phenol Using a Sodium Methoxide Catalyst

The reactor employed in Example 1 was charged with 685 grams (3.0 moles) of Bisphenol "A", 546 grams (6.2 moles) of Propylene carbonate and 2.31 grams of sodium methoxide in methanol (25% concentration). Under stirring, the temperature was increased up to 180° C. The reaction was followed by titration of the phenol and stopped until completion. The Brookfield viscosity of the hydroxyalkylated phenol was determined using standard procedure at 40° C. to be about 40 poise.

EXAMPLE 3

Preparation of a Hydroxyalkylated Phenol Using a Sodium Methoxide Catalyst

A 500 ml reactor was charged with 2,488 grams (14.62 moles) of 4-phenyl phenol, 1,415 grams (16.0 moles) of ethylene carbonate and 3.9 grams of sodium methoxide in methanol (25% concentration). The reaction was carried out at 180° C. The formation of the hydroxyethyl derivative was followed by titration and the reaction stopped until no more free phenol was detected. Characterization was done by $H^1$ NMR. The melting point of the resulting hydroxyalkylated phenol was measured utilizing standard procedure and was determined to be 122.5° C.

EXAMPLE 4

Preparation of Hydroxyalkylated Nonyl Phenol Using Sodium Methoxide Catalyst

A 5000 ml reactor was charged with 2203.60 grams (10 moles) of nonyl phenol, 888.80 grams (10.10 moles) of ethylene carbonate, and 1.24 grams of sodium methoxide. The reaction was carried out at a temperature of 180° C. The formation of the hydroxyethyl derivative was followed by titration and the reaction was stopped when no more free phenol was detected. Characterization was done by $H_1$ NME. The product had a Brookfield viscosity of 650 cps at 25° C.

EXAMPLE 5

Preparation of Hydroxyalkylated Mixtures of Phenols Using Sodium Methoxide Catalyst A 2000 ml reactor was charged with 612.8 grams (3.6 moles) of phenyl phenol, 88.0 grams (0.4 moles) of nonyl phenol, 369.6 grams (4.2 moles) of ethylene carbonate, and 0.21 grams of sodium methoxide. The reaction was carried out at a temperature of 180° C. The formation of the hydroxyethyl intermediates was followed by titration and the reaction stopped until no more free phenol was detected. The product had a melting point of 105.0° C. and a crystallization temperature of 93.0° C.

The invention has been described in detail with reference to its preferred embodiments and its examples. However, it will be apparent that numerous variations and modifications can be made without departure from the spirit and scope of the invention as described in the foregoing detailed specification and claims.

That which is claimed:

1. In a process for the preparation of a hydroxyalkylated phenolic or hydroxyalkylated thiophenolic compound wherein a phenolic or thiophenolic compound is reacted with a cyclic organic carbonate in the presence of a catalyst, the improvement comprising wherein said catalyst is selected from the group consisting of an alkali metal, an alkali metal alkoxide, and mixtures thereof.

2. The process according to claim 1 wherein the alkali metal is selected from the group consisting of sodium, potassium, and lithium.

3. The process according to claim 1 wherein the alkali metal alkoxide is a methoxide or ethoxide salt.

4. The process according to claim 1 wherein the phenolic or thiophenolic compound is selected from the group consisting of phenol, β-naphthol, p,p'-sec-butylidenediphenol, o-chloro phenol, o-cresol, p-propyl phenol, p-bis(o-cresol), phenyl phenol, thiophenol, o-thiocresol, m-thiocresol, p-thiocresol, 4,4'-thiodiphenol, 4,4'-thiobisbenzenethiol, hydroxyquinoline, catechol, resorcinol, hydroquinone, 4,4'-biphenol, 4,4'-isopropylidenebis(o-cresol), 4,4'-isopropylidenebis(2-phenyl phenol), bisphenol A, nonyl phenol, pyrogallol, phloroglucinol, and mixtures thereof.

5. The process according to claim 1 wherein the cyclic organic carbonate compound is selected from the group consisting of propylene carbonate, 1,2-butylene carbonate, 2,3-butylene carbonate, phenylethylene carbonate, and mixtures thereof.

6. The process according to claim 1 wherein said step of reacting the phenolic or thiophenolic compound and the cyclic organic carbonate compound is carried out at a temperature of from about 100° C. to 220° C.

7. A process for the preparation of a hydroxyalkylated phenolic or hydroxyalkylated thiophenolic compound comprising:

providing a phenolic or thiophenolic compound, a cyclic organic carbonate compound, and from about 0.0005 to 3.0 percent by weight of a catalyst selected from the group consisting of an alkali metal, an alkoxide, and mixtures thereof, wherein the cyclic organic carbonate compound is present in an amount from about 1.02 to 1.5 moles per every hydroxy or thiol group present in the phenolic or thiophenolic compound; and reacting the phenolic or thiophenolic compound and the cyclic organic carbonate compound in the presence of the catalyst to form the hydroxyalkylated phenolic or hydroxyalkylated thiophenolic compound.

8. The process according to claim 7 wherein the alkali metal is selected from the group consisting of sodium, potassium, and lithium.

9. The process according to claim 7 wherein the alkali metal alkoxide is a methoxide or ethoxide salt.

10. The process according to claim 7 wherein the phenolic or thiophenolic compound is selected from the group consisting of phenol, β-naphthol, p,p'-sec-butylidenediphenol, o-chloro phenol, o-cresol, p-propyl phenol, p-bis(o-cresol), phenyl phenol, thiophenol, o-thiocresol, m-thiocresol, p-thiocresol, 4,4'-thiodiphenol, 4,4'-thiobisbenzenethiol, hydroxyquinoline, catechol, resorcinol, hydroquinone, 4,4'-biphenol, 4,4'-isopropylidenebis(o-cresol), 4,4'-isopropylidenebis (2-phenyl phenol), bisphenol A, nonyl phenol, pyrogallol, phloroglucinol, and mixtures thereof.

11. The process according to claim 7 wherein the cyclic organic carbonate compound is selected from the group consisting of propylene carbonate, 1,2-butylene carbonate, 2,3-butylene carbonate, phenylethylene carbonate, and mixtures thereof.

12. The process according to claim 7 wherein said step of reacting the phenolic or thiophenolic compound and the cyclic organic carbonate compound is carried out at a temperature of from about 100° C. to 220° C.

* * * * *

UNITED STATES PATENT AND TRADEMARK OFFICE
CERTIFICATE OF CORRECTION

PATENT NO. : 5,679,871
DATED : October 21, 1997
INVENTOR(S) : Hildeberto Nava

It is certified that error appears in the above-identified patent and that said Letters Patent is hereby corrected as shown below:

Col. 3, Line 12 insert a space before "diphenol".

Claim 4, Col. 6, Line55, insert a space before "diphenol".

Claim 7, Col. 7, Line 11, delete "alkali metal, an alkoxide," should read --alkali metal, an alkali metal alkoxide,--.

Claim 10, Col. 8, Line 5, insert a space before "diphenol".

Signed and Sealed this

Fourteenth Day of April, 1998

Attest:

BRUCE LEHMAN

*Attesting Officer*        *Commissioner of Patents and Trademarks*